United States Patent [19]

Weiss

[11] 4,449,926
[45] May 22, 1984

[54] DENTAL ELECTROSURGERY ELECTRODES AND METHOD OF USE

[76] Inventor: Peter A. Weiss, 501 Greendale Ave., Needham, Mass. 02192

[21] Appl. No.: 323,804

[22] Filed: Nov. 23, 1981

Related U.S. Application Data

[63] Continuation of Ser. No. 183,035, Sep. 2, 1980, abandoned.

[51] Int. Cl.³ .................................................. A61C 3/00
[52] U.S. Cl. ........................................ 433/32; 433/218
[58] Field of Search ........................ 433/32, 215, 218; 128/303.1, 303.13, 303.14, 303.15, 303.16, 303.17

[56] References Cited

U.S. PATENT DOCUMENTS

| 1,071,978 | 9/1913 | White | 128/303.13 |
| 1,735,271 | 11/1929 | Groff | 128/303.14 |
| 1,770,653 | 7/1930 | Molony | 128/303.17 |
| 2,012,316 | 8/1935 | Miles | 128/303.14 |
| 3,215,139 | 11/1965 | Dietz | 433/32 |
| 3,295,514 | 1/1967 | Hein et al. | 433/32 |
| 3,920,021 | 11/1975 | Hiltebrandt | 128/303.17 |
| 3,970,088 | 7/1976 | Morrison | 128/303.14 |
| 4,274,413 | 6/1981 | Hahn et al. | 128/303.17 |

Primary Examiner—John J. Wilson
Attorney, Agent, or Firm—Wolf, Greenfield & Sacks

[57] ABSTRACT

Electrosurgery electrodes for dentistry which are partially insulated on their radiating surfaces in such a manner that, in use, only the lateral wall of the sulcus is affected. The insulated portion of the electrode can safely be brought into contact with the tooth which is used as a guide.

9 Claims, 7 Drawing Figures

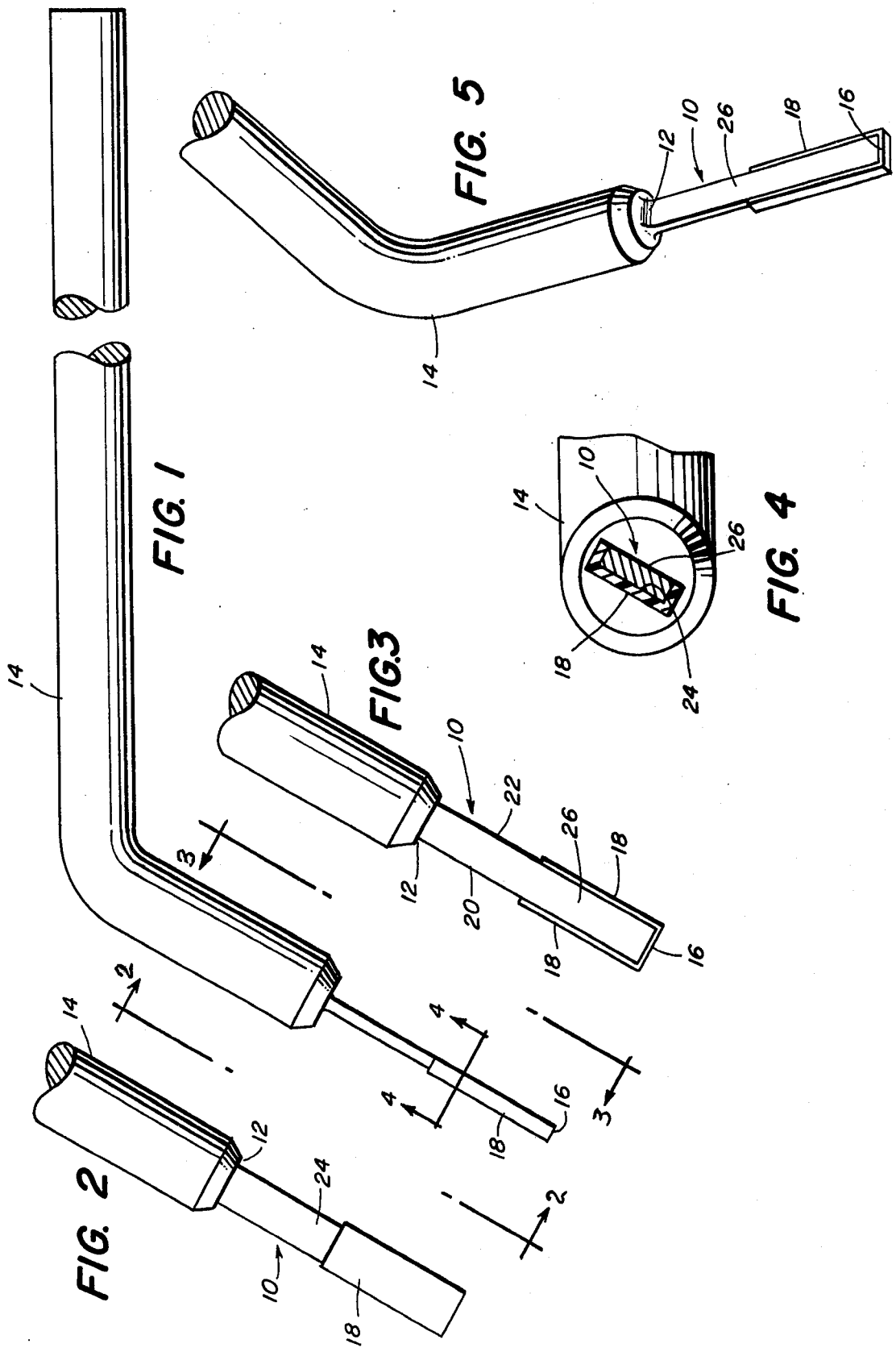

DENTAL ELECTROSURGERY ELECTRODES AND METHOD OF USE

This is a continuation of application Ser. No. 183,035, filed Sept. 2, 1980, now abandoned.

BACKGROUND OF THE INVENTION

In order to achieve acceptable esthetics and provide protection from decay the margins of crowns and inlays are placed into the gum groove or sulcus. Fabrication of the crowns and inlays is accomplished on replicas of properly prepared teeth which are made from impressions rendered in a variety of materials. In order that these impressions register the end or finish lines of said crowns or inlays the gum margin must be temporarily retracted. Two methods are in common use: packing with cord and electrosurgery. The latter has many advantages but execution with existing electrodes is subject to a severe limitation which does not allow the technique to realize its potential and makes it essentially destructive and unpredictable.

The problem involves the following impasse: in order to get any tactile feedback the tooth must be used as a guide. However, any contact with the tooth incinerates the surface of the cementum, and destroys the epithelial attachment—the connection of the gum to the tooth root.

GENERAL NATURE OF THE INVENTION

I propose to provide electrosurgery electrodes which are partially insulated on their radiating surfaces in such manner that, in use, only the lateral wall of the sulcus is affected. The insulated portion of the electrode can be safely brought into contact with the tooth which is used as a guide. Such instruments are also vertically self limiting, protecting the epithelial attachment. Embodiments of the invention and advantages in use are described in greater detail with reference to the accompanying drawing.

THE PRIOR ART

In a search conducted in Class 128, Subclasses 303.1, 303.13, and 303.17; and in Class 433, Subclass 32 (cursory), the following patents were noted:

Jamshidi U.S. Pat. No. 3,886,944 shows a microcautery device which localizes heat at a tip by making the metal of the tip thinner than in the supporting shaft.

Starr U.S. Pat. No. 300,155 shows a cauterizing needle for root canal work, and (FIG. 6) a surgical knife.

Kidder U.S. Pat. No. 164,183 shows a handle with finger rings.

Werner U.S. Pat. No. 3,301,258 heats tissue with bi-polar electrodes 10, 15. Webb U.S. Pat. No. 2,100,116 is similar.

Bobb U.S. Pat. No. 3,234,356 shows a bead of glass, etc., for applying heat. It extends out from the heating wire 90.

Miller U.S. Pat. No. 3,532,095 shows a ball tip for contacting the tissue, and an insulating sleeve 36 around the shaft 34 of the ball. The insulator is used to fix the length of the shaft 34, and to protect the surgeon.

None discloses an instrument which would satisfy my purpose; in fact, the instruments described in these patents are subject to the above-related impasse.

BRIEF DESCRIPTION OF THE DRAWINGS

FIG. 1 is a side view, on an enlarged scale, of an electrosurgery tip for dentistry according to the invention;

FIG. 2 is a partial side view of the tip in FIG. 1, viewed from line 2—2;

FIG. 3 is a partial side view of the tip in FIG. 1, viewed from line 3—3;

FIG. 4 is a section on line 4—4 of FIG. 1;

FIG. 5 is an isometric view of the tip shown in FIG. 1;

DETAILED DESCRIPTION OF THE DRAWINGS

Figure 6:
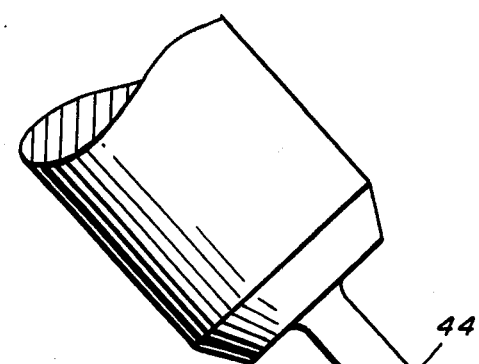
FIG. 6 is a side view of another electrosurgery tip for dentistry according to the invention.

The dental electrosurgery tip 10 shown in FIGS. 1-5, inclusive, has a rectangular cross-section, typically about 0.25 mm. thick, and 1.00 mm. wide. The tip is about 25 mm. long, and is held at an end 12 in a handle 14. About one-half of the tip, from its free end 16 toward the handle end 12, is coated with an insulator 18 on both narrow sides 20, 22, one wide side 24 and the free end 16. The remaining wide side 26 of the tip is not covered by the insulator 18.

Figure 7:
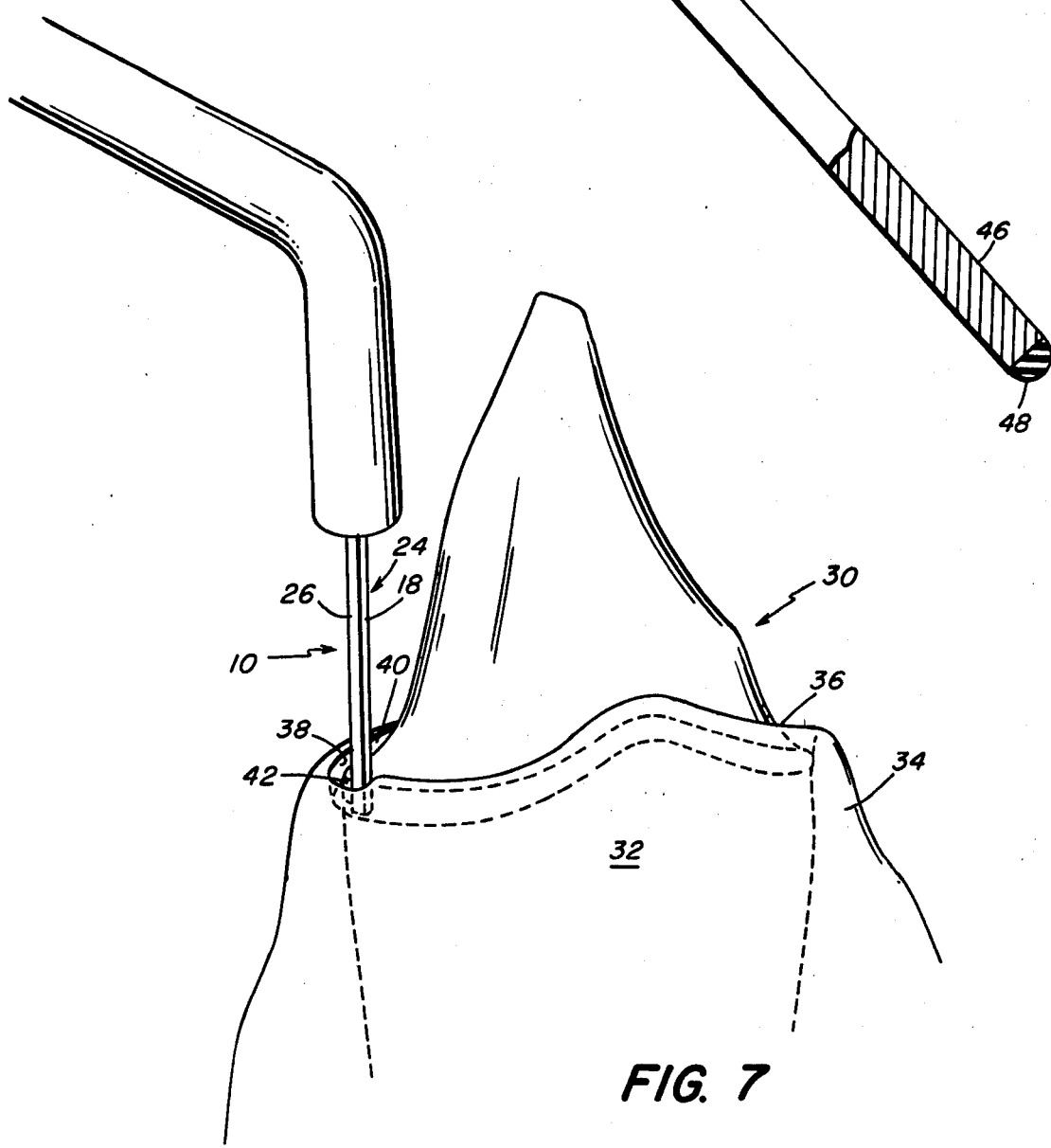
FIG. 7 is an enlarged schematic drawing showing the tip of FIG. 1 in use.

In use, the electrosurgery tip 10 is employed to remove tissue around a tooth, in a manner that is illustrated in FIG. 7. In FIG. 7, a tooth 30 has a root portion 32 surrounded by gum tissue 34 at the gum margin 36. The electrosurgery tip is placed in the sulcus at the margin 36, with the insulation 18 in contact with the tooth 30, and the non-insulated side 26 toward the gum tissue 34. The uninsulated side 26 of the tip 10 presents a radiating surface to the lateral wall 38 of the sulcus which is formed of gum tissue 34, forming a thin groove 40 in the gum tissue. The opposite side 24 of the tip 10 is covered by the insulation 18, and so can not incinerate the surface 42 of the cementum of the tooth 30, which now can safely be used as a guide for the tip 10 in making the groove 40 in the tissue 34 around the tooth at the margin 36. Typically, it is desired to make a one-quarter millimeter wide gum groove 40 around the tooth.

FIG. 6 illustrates an electrosurgery tip 44 that is useful for touch-up purposes. This tip 44 has a round cross section, about one-quarter millimeter in diameter, and is fitted at its extremity 46 with an insulator 48 that is rounded on a radius about 0.125 mm.

The surfaces of the electrode and covering insulator should preferably be smooth, or polished, to avoid catching the tissue 38 of the sulcus or on the guiding surface 42 of the tooth 30. The electrode may be made, for example of a nickle-chronium alloy; while the insulator may be made of a thin layer of a ceramic material.

I claim:

1. An electrosurgery tip for dental use for forming a uniform thin groove in the gum groove that is naturally defined about a tooth to receive the margin of crowns or inlays and comprising a metallic tip having on a limited portion of its radiating surfaces an electrical insulation material for providing a non-incinerating contact between the tip and tooth, whereby when the electrosurgery tip is placed in the gum groove the insulation material is in contact with the associated tooth, whereby the incinerating surface or surfaces of the tip can be guided by contact of the non-incinerating surface with and relative to said tooth in a desired path of incineration without causing incineration of said tooth, said incinerating surface or surfaces presenting a radiating surface to the lateral wall of the gum groove to form the uniform thin groove about the periphery of the tooth meant to receive the margin of the crown or inlay, said tip being of about one-quarter millimeter thickness to thus form the uniform thin groove of like width, said radiating and insulating surfaces of the tip being substantially oppositely faced.

2. An electrosurgery tip according to claim 1 wherein said tip has a rectangular cross section with four sides and a free end and covered on three sides and its free end with said insulation, the fourth side of said tip being free of insulation.

3. An electrosurgery tip according to claim 1 in which said fourth side is a wide side of said tip.

4. An electrosurgery tip according to claim 3 in which said tip is about one millimeter wide.

5. An electrosurgery tip according to claim 1 in which said tip is rounded in cross-section.

6. An electrosurgery tip according to claim 5 in which said tip has a diameter about one-quarter millimeter.

7. An electrosurgery tip according to claim 5 in which said tip has a diameter about one-quarter millimeter, and said insulation is curved on a radius about one-eight millimeter.

8. A method used in dental applications to form a thin groove in the gum groove naturally disposed about a tooth employing an electrosurgery tip, said uniform thin groove for receiving the margin of crowns, inlays or the like, comprising the steps of, providing a metallic tip having on a limited portion of its radiating surfaces an electrical insulation material for providing non-incinerating contact between the tip and tooth, placing the electrosurgery tip in the gum groove with the tip oriented so that the insulation material is in contact with the associated tooth, concurrently placing the tip so that the radiating surface is presented to the lateral wall of the gum groove, and guiding said tip thus oriented in a path of incineration about the tooth along the gum groove without causing incineration of the tooth itself to thus form the uniform thin groove about the periphery of the tooth.

9. A method as set forth in claim 8 including providing a tip of thickness to provide a uniform groove of about one-quarter millimeter.

* * * * *